(12) United States Patent
Ikoma

(10) Patent No.: US 11,684,748 B2
(45) Date of Patent: Jun. 27, 2023

(54) CATHETER AND METHOD FOR PRODUCING SAME

(71) Applicant: KANEKA CORPORATION, Osaka (JP)

(72) Inventor: Kazuaki Ikoma, Osaka (JP)

(73) Assignee: KANEKA CORPORATION, Osaka (JP)

( * ) Notice: Subject to any disclaimer, the term of this patent is extended or adjusted under 35 U.S.C. 154(b) by 159 days.

(21) Appl. No.: 16/957,641

(22) PCT Filed: Dec. 13, 2018

(86) PCT No.: PCT/JP2018/045813
§ 371 (c)(1),
(2) Date: Jun. 24, 2020

(87) PCT Pub. No.: WO2019/131158
PCT Pub. Date: Jul. 4, 2019

(65) Prior Publication Data
US 2021/0052850 A1    Feb. 25, 2021

(30) Foreign Application Priority Data
Dec. 27, 2017   (JP) ............................ JP2017-251953

(51) Int. Cl.
*A61M 25/00*       (2006.01)
*A61M 25/01*       (2006.01)
(Continued)

(52) U.S. Cl.
CPC ....... *A61M 25/0045* (2013.01); *A61L 29/049* (2013.01); *A61M 25/0009* (2013.01);
(Continued)

(58) Field of Classification Search
CPC .......... A61M 25/0045; A61M 25/0026; A61M 25/10; A61M 25/0009; A61M 25/0102;
(Continued)

(56) References Cited

U.S. PATENT DOCUMENTS 5,415,636 A * 5/1995 Forman ............... A61M 25/104
604/101.03
5,772,632 A    6/1998 Forman
(Continued)

FOREIGN PATENT DOCUMENTS

JP    H09-505503 A    6/1997
JP    H10-305093 A    11/1998
(Continued)

OTHER PUBLICATIONS

Japanese to English Machine translation of the specification of JP-2004033354-A (Year: 2004).*
(Continued)

*Primary Examiner* — Katherine H Schwiker
*Assistant Examiner* — Robert F Allen
(74) *Attorney, Agent, or Firm* — Osha Bergman Watanabe & Burton LLP

(57) ABSTRACT

A catheter may include a distal side and a proximal side comprising a shaft having an outer tubular member, and an insertion member. The catheter may have at least a part of the insertion member in an axial direction disposed in the outer tubular member. At least one outer tubular member or insertion member is a multilayer tube having a first layer and a second layer laminated with the first layer. In a cross-section perpendicular to an axial direction of the multilayer tube, a ratio of cross-sectional areas of the second layer to the first layer is 0.7 or less.

19 Claims, 8 Drawing Sheets

(51) Int. Cl.
*A61L 29/14* (2006.01)
*A61M 25/10* (2013.01)
*A61M 25/09* (2006.01)
*A61L 29/04* (2006.01)

(52) U.S. Cl.
CPC .... *A61M 25/0026* (2013.01); *A61M 25/0102* (2013.01); *A61M 25/09* (2013.01); *A61M 25/10* (2013.01); *A61L 29/14* (2013.01)

(58) Field of Classification Search
CPC ............... A61M 25/09; A61M 25/005; A61M 25/1036; A61M 25/104; A61M 2025/0059; A61M 25/0012; A61L 29/049; A61L 29/14
See application file for complete search history.

(56) References Cited

U.S. PATENT DOCUMENTS

| | | | |
|---|---|---|---|
| 6,010,521 A * | 1/2000 | Lee .................. | A61M 25/0009 606/194 |
| 6,165,166 A | 12/2000 | Samuelson et al. | |
| 6,960,186 B1 * | 11/2005 | Fukaya ............. | A61M 25/1027 604/103.06 |
| 6,977,105 B1 * | 12/2005 | Fujieda ................ | A61L 29/126 428/36.9 |
| 2003/0014008 A1 * | 1/2003 | Jacques ............. | A61M 25/0032 600/431 |
| 2005/0142314 A1 * | 6/2005 | Burgmeier ............ | A61L 29/14 264/211 |
| 2005/0233062 A1 * | 10/2005 | Hossainy .................. | A61F 2/91 427/2.1 |
| 2005/0288628 A1 | 12/2005 | Jordan et al. | |
| 2006/0030835 A1 | 2/2006 | Sherman et al. | |
| 2007/0141112 A1 * | 6/2007 | Falotico .................. | A61L 27/34 424/426 |
| 2014/0276401 A1 * | 9/2014 | Lee .......................... | A61L 29/06 604/96.01 |
| 2015/0190624 A1 * | 7/2015 | Jeon ...................... | A61L 31/048 604/264 |
| 2015/0283357 A1 * | 10/2015 | Lampropoulos .... | B32B 37/0038 604/523 |
| 2016/0339211 A1 | 11/2016 | Lee et al. | |
| 2020/0061352 A1 * | 2/2020 | Suzuki ................ | B29C 65/1674 |

FOREIGN PATENT DOCUMENTS

| | | | | |
|---|---|---|---|---|
| JP | 2004-33354 | A | | 2/2004 |
| JP | 2004033354 | A | * | 2/2004 |
| JP | 2007-29736 | A | | 2/2007 |
| JP | 2007-236633 | A | | 9/2007 |
| JP | 2007236633 | A | * | 9/2007 |
| JP | 2018-011953 | A | | 1/2018 |

OTHER PUBLICATIONS

Extended European Search Report issued in corresponding European Application No. 18897817.5 dated Sep. 23, 2021 (8 pages).
International Search Report issued in International Application No. PCT/JP2018/045813, dated Mar. 12, 2019 (1 page).
Written Opinion issued in International Application No. PCT/JP2018/045813, dated Mar. 12, 2019 (5 pages).

* cited by examiner

[FIG. 1]
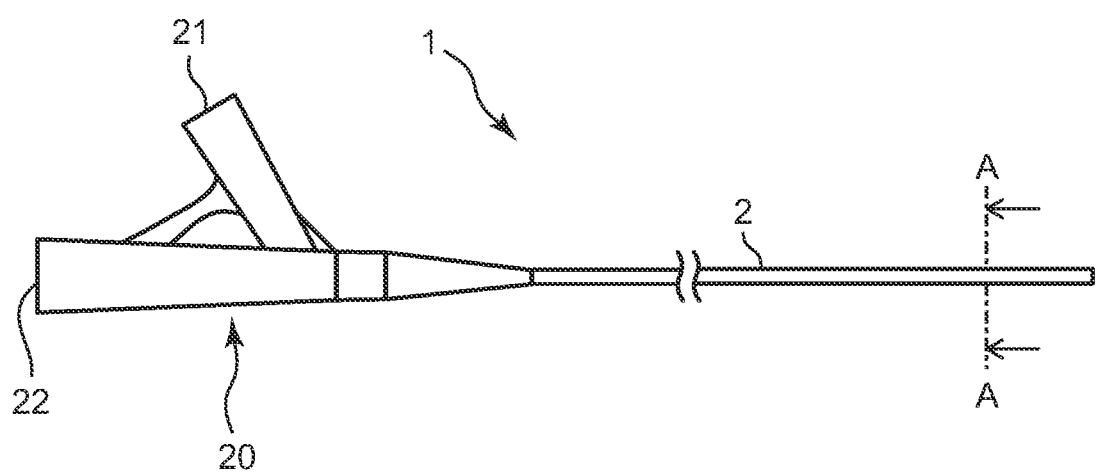

[FIG. 2]
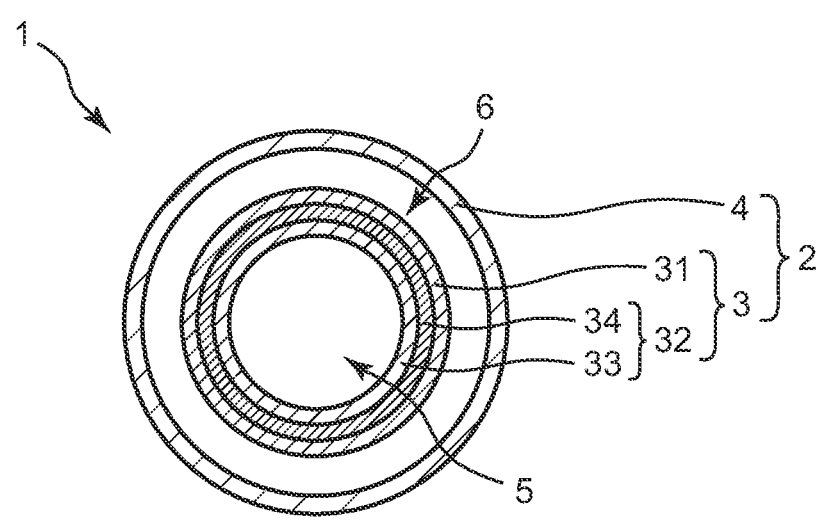

[FIG. 3]
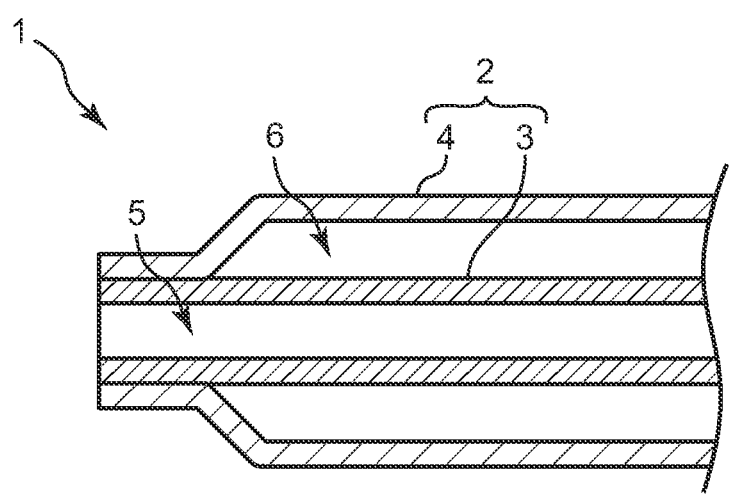

[FIG. 4]
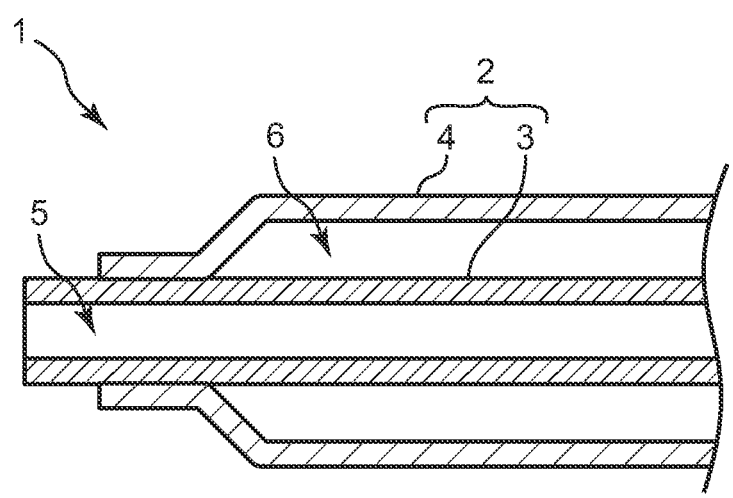

[FIG. 5]
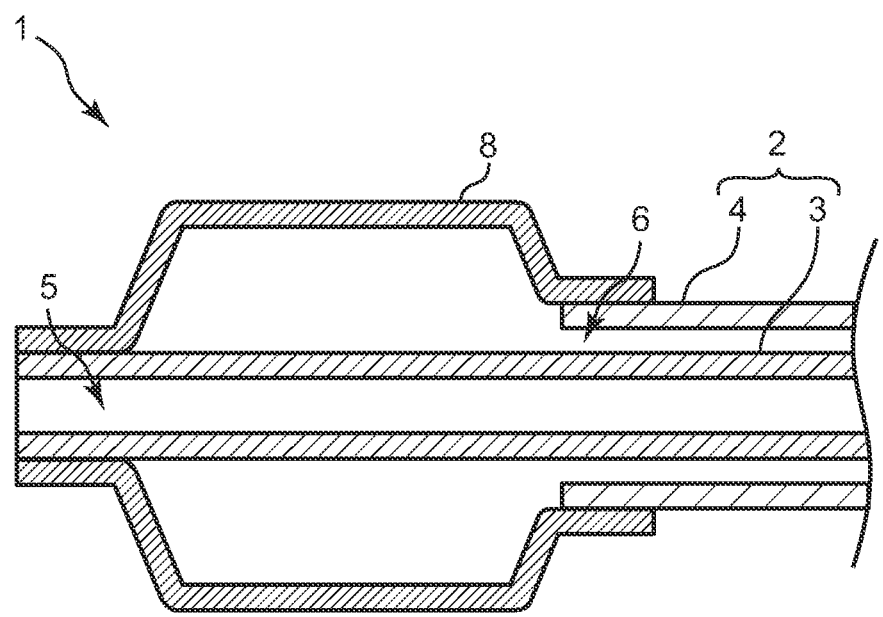

[FIG. 6]
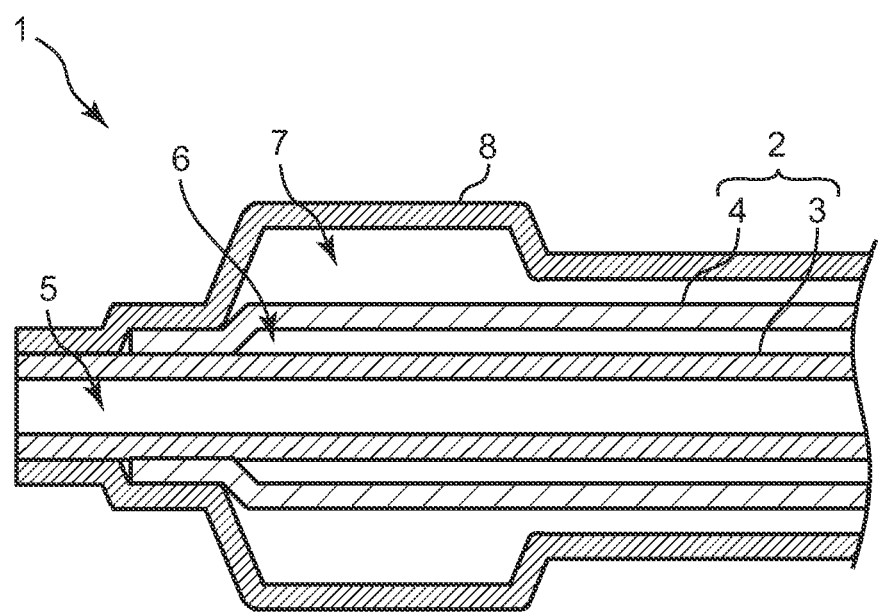

[FIG. 7]
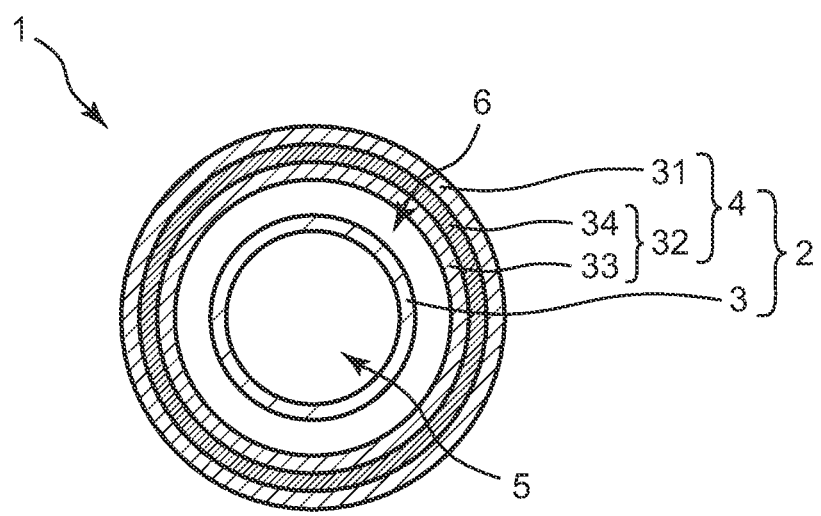

[FIG. 8]
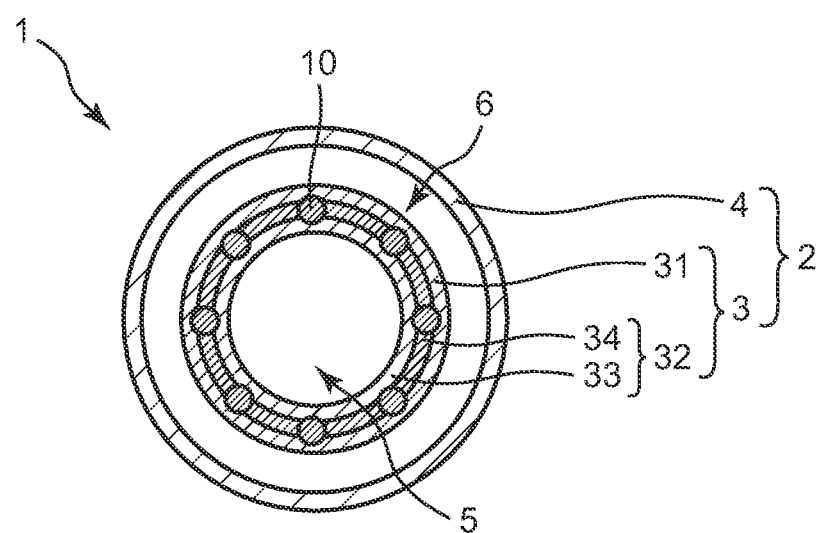

CATHETER AND METHOD FOR PRODUCING SAME

TECHNICAL FIELD

One or more embodiments of the present disclosure relate to a catheter in which includes an outer tubular member and an insertion member and a method for producing the same. At least one of the outer tubular member or the insertion member is a multilayer tube having a first layer and a second layer laminated with the first layer.

BACKGROUND

It has been known that various diseases are caused by stagnant circulation of blood due to constriction of a blood vessel, which is a flow path through which blood is circulated in the body. Particularly when a coronary artery supplying blood to the heart becomes stenosed, serious diseases such as angina or myocardial infarction may be caused. As one of methods for treating such a stenosed part of a blood vessel, angioplasty (for example, PTA and PTCA) has been used for dilating the stenosed part using a balloon catheter or a stent. Angioplasty is a minimally invasive therapy that does not require thoracotomy, such as bypass surgery, thus is widely used.

In angioplasty, a preliminary step for the expansion of the stenosed part with a balloon catheter or a stent requires insertion of a guide wire into a lesion. For this purpose, there is a catheter including a tubular shaft into whose lumen a guide wire can be inserted. This catheter is required to have excellent slidability between the lumen of the shaft and the guide wire and excellent passability of guide wire. The catheter is also required to have flexibility so that it is unlikely to physically stimulate an inner wall of a blood vessel or the like. Such a catheter is exemplified by one including a shaft having an inner layer and an outer layer (for example, see Patent Documents 1 and 2).

PATENT DOCUMENTS

Patent Document 1: JP-A-2004-33354
Patent Document 2: JP-A-2007-29736

However, the conventional catheters disclosed in Patent Documents 1 and 2, a shaft is flattened when the catheter is pressurized for such as to expand a balloon. This flattened shaft in some cases deteriorates slidability with a guide wire, which is inserted into a lumen of the shaft, and with a member disposed outside the shaft in a radial direction. In a cross-section perpendicular to an axial direction of a shaft, it has been found that when a roundness (initial roundness) of the cross sectional shape of the shaft before using a catheter is low, the shaft is likely to be flat, and the slidability of the shaft tends to be low.

SUMMARY

One or more embodiments of the present disclosure is to provide a catheter which is excellent in slidability and a shaft is hardly flattened after pressurization, and to provide a method for producing the catheter.

A catheter of one or more embodiments of the present disclosure has a distal side and a proximal side comprising:
a shaft having an outer tubular member, and
an insertion member wherein at least a part of the insertion member in an axial direction thereof is disposed in the outer tubular member,
at least one of the outer tubular member or the insertion member is a multilayer tube having a first layer and a second layer laminated with the first layer,
in a cross-section perpendicular to an axial direction of the multilayer tube, a ratio of a cross-sectional area of the second layer to a cross-sectional area of the first layer (a cross-sectional area of the second layer/a cross-sectional area of the first layer) is 0.7 or less,
a material constituting the second layer has a higher crystallinity degree than that of a material constituting the first layer,
a material constituting the second layer has a lower melting point than that of a material constituting the first layer, and
in the cross-section perpendicular to the axial direction of the multilayer tube, an initial roundness calculated by the following equation (1) is 92% or more.

$$\text{initial roundness (\%)}=(\text{a minor axis outer diameter of the multilayer tube/a major axis outer diameter of the multilayer tube})\times 100 \quad (1)$$

In the catheter of one or more embodiments of the present disclosure, the second layer may be disposed more inside in a radial direction than the first layer.

In the catheter of one or more embodiments of the present disclosure, the insertion member may be the multilayer tube.

In the catheter of one or more embodiments of the present disclosure, the insertion member may have a first lumen into which a guide wire is inserted.

In the catheter of one or more embodiments of the present disclosure, the shaft may have a second lumen into which a fluid is supplied between the outside of the insertion member and the inside of the outer tubular member.

In the catheter of one or more embodiments of the present disclosure, in a cross-section perpendicular to the axial direction of the insertion member, after the following pressure test, a roundness of the insertion member after the pressure test calculated by the following equation (2) is 75% or more.

(Pressure Test)
(i) disposing a core material within the first lumen,
(ii) placing the catheter under a 1 atm (atmospheric pressure) and 37° C. water environment,
(iii) applying pressure of rated burst pressure (RBP)+1 atm (atmospheric pressure) to within the second lumen for 30 seconds,
(iv) depressurizing the pressure within the second lumen to 1 atm (atmospheric pressure), and
(v) repeating the above (iii) to (iv) 20 times $$\text{roundness after pressure test (\%)}=(\text{a minor axis outer diameter of the insertion member after the pressure test/a major axis outer diameter of the insertion member after the pressure test})\times 100 \quad (2)$$

wherein the minor axis outer diameter and the major axis outer diameter of the insertion member after the pressure test are measured at the same point where the minor axis outer diameter and the major axis outer diameter of the insertion member are measured upon the calculation of the initial roundness.

In the catheter of one or more embodiments of the present disclosure, when the fluid is supplied with the rated burst pressure (RBP) into the second lumen, an outer diameter reduction rate of the insertion member at a point where an outer diameter of the insertion member becomes smallest is within 10%.

In the catheter of one or more embodiments of the present disclosure, the point where the outer diameter of the insertion member becomes smallest may be inside the second lumen.

In the catheter of one or more embodiments of the present disclosure, the second lumen may be provided on the distal side of the shaft.

The catheter of one or more embodiments of the present disclosure may comprise a balloon connected on the distal side of the second lumen.

In the catheter of one or more embodiments of the present disclosure, the shaft has a third lumen into which a fluid is supplied, and the catheter has a balloon, which is connected to the third lumen on the distal side of the shaft.

In the catheter of one or more embodiments of the present disclosure, a ratio of a Shore hardness of the material constituting the first layer to a Shore hardness of the material constituting the second layer (a Shore hardness of the material constituting the first layer/a Shore hardness of the material constituting the second layer) may be 0.9 or more.

In the catheter of one or more embodiments of the present disclosure, the material constituting the first layer and the material constituting the second layer may be a thermoplastic resin.

In the catheter of one or more embodiments of the present disclosure, the material constituting the first layer may be a polyamide-based resin.

In the catheter of one or more embodiments of the present disclosure, the material constituting the second layer may be a polyolefin-based resin.

In the catheter of one or more embodiments of the present disclosure, the polyolefin-based resin may be a high-density polyethylene resin or a polypropylene resin.

In the catheter of one or more embodiments of the present disclosure, the second layer may have a layer A, and a layer B laminated with the layer A. The layer B may join the first layer and the layer A.

In the catheter of one or more embodiments of the present disclosure, a material constituting the layer B may be a linear low-density polyethylene resin.

In the catheter of one or more embodiments of the present disclosure, the outer tubular member and the insertion member may be relatively movable in a distal and proximal direction.

A method for producing the catheter of one or more embodiments of the present disclosure may comprise a step of producing by co-extrusion molding the multilayer tube having the first layer and the second layer laminated with the first layer.

The catheter of one or more embodiments of the present disclosure can improve slidability between the outer tubular member and the insertion member or between the insertion member and the guide wire. In addition, the catheter can prevent the shaft from flattening after pressurization.

BRIEF DESCRIPTION OF THE DRAWINGS

FIG. 1 is a plan view of a catheter according to one or more embodiments of the present disclosure.

FIG. 2 is a cross-sectional view showing the catheter in FIG. 1 that is taken along line A-A according to one or more embodiments.

FIG. 3 is a cross-sectional view showing a catheter that is taken along an axial direction thereof according to one or more embodiments.

FIG. 4 is a cross-sectional view showing another example of the catheter in FIG. 3 that is taken along the axial direction thereof according to one or more embodiments.

FIG. 5 is a cross-sectional view showing yet another example of the catheter in FIG. 3 that is taken along the axial direction thereof according to one or more embodiments.

FIG. 6 is a cross-sectional view of still yet another example of the catheter in FIG. 3 that is taken along the axial direction thereof according to one or more embodiments.

FIG. 7 is a cross-sectional view showing another example of the catheter in FIG. 2 according to one or more embodiments.

FIG. 8 is a cross-sectional view showing yet another example of the catheter in FIG. 2 according to one or more embodiments.

DETAILED DESCRIPTION

One or more embodiments of the present disclosure will be explained below based on the following embodiments, however, one or more embodiments of the present disclosure is not restricted by the embodiments described below and can be put into practice after appropriate modifications within a range meeting the embodiments of the above and the below, all of which are included in the technical scope of one or more embodiments of the present disclosure. In the drawings, hatching, a reference sign for a member may be omitted for convenience, and in such a case, the description and other drawings should be referred to. In addition, sizes of various members in the drawings may differ from the actual sizes thereof, since priority is given to understanding the features of one or more embodiments of the present disclosure. In the one or more embodiments of present description, pressure that is applied to a catheter is expressed as absolute pressure.

Firstly, described is an entire structure of the catheter with FIG. 1 and FIG. 2 as references. FIG. 1 is a plan view showing the catheter of one or more embodiments of the present disclosure, and FIG. 2 is a cross-sectional view showing the catheter in FIG. 1 that is taken along line II-II. FIG. 1 shows a configuration example of a catheter which a guide wire (hereinafter may be referred to as simply "GW") is inserted into a shaft from a proximal side to a distal side, which is so-called over-the-wire catheter.

The catheter 1 has a proximal side and a distal side. In one or more embodiments of the present disclosure, the proximal side of the catheter 1 refers to a direction of a hand side of a user (operator) against an extension direction of the catheter 1, and the distal side refers to an opposite direction to the proximal side (that is, a direction of a treatment target side). In addition, a direction from the proximal side to the distal side of the catheter 1 is referred to as an axial direction.

The catheter 1 includes a shaft 2 having an outer tubular member 4 and an insertion member 3, and at least a part of the insertion member 3 in an axial direction thereof is disposed in the outer tubular member 4. The insertion member 3 may be a tubular shape similar to the outer tubular member 4 or may be a solid column shape. In a case where the insertion member 3 is the tubular shape, a guide wire may be inserted into a lumen thereof.

At least one of the outer tubular member 4 or the insertion member 3 is a multilayer tube having a first layer 31 and a second layer 32 laminated with the first layer 31. That is, as shown in FIGS. 2 and 7, either the insertion member 3 or the outer tubular member 4 may be the multilayer tube, or, though not illustrated, both the insertion member 3 and the outer tubular member 4 may be the multilayer tubes.

A material constituting the second layer 32 has a higher crystallinity degree than that of a material constituting the first layer 31. Furthermore, at least one material included in the second layer 32 may have a higher crystallinity degree than that of at least one material included in the first layer 31. In addition, a material constituting the second layer 32 has a lower melting point than that of a material constituting the first layer 31. Furthermore, at least one material included in the second layer 32 in one or more embodiments may have a lower melting point than that of at least one material included in the first layer 31. This composition of the first layer 31 and the second layer 32 lowers a coefficient of friction on a contact surface between the insertion member 3 and the outer tubular member 4. Examples of a method for measuring the crystallinity degrees of the material constituting in the first layer 31 and the material constituting in the second layer 32 include densimetry, X-ray analysis, infrared spectroscopy, Raman spectroscopy, differential scanning calorimetry (DSC).

The material constituting the second layer 32 merely needs to have a higher crystallinity degree than that of the material constituting the first layer 31, and may be no limitation is given to a crystallinity degree ratio of the material constituting the second layer 32 to the material constituting the first layer 31. However, for example, the material constituting the second layer 32 has the crystallinity degree in one or more embodiments that may be 1.3 times or more, 2.0 times or more, and further 3.0 times or more as high as that of the material constituting the first layer 31. Setting the lower limit of the crystallinity degree ratio of the material constituting the second layer 32 to the material constituting the first layer 31 to be within the above range can enhance tube hardness of the multilayer tube upon production thereof. The upper limit of the crystallinity degree ratio of the material constituting the second layer 32 to the material constituting the first layer 31 in one or more embodiments may be 10 times or less, 9 times or less, and further 8 times or less. Setting the upper limit of the crystallinity degree ratio of the material constituting the second layer 32 to the material constituting the first layer 31 to be within the above range can reduce quench distortion and heat shrinkage of the multilayer tube upon production thereof, thus enabling flattening prevention to a great degree.

The material constituting the second layer 32 merely needs to include a lower melting point (° C.) than that of the material constituting the first layer 31. Especially, a melting point (° C.) ratio of the material constituting the second layer 32 to the material constituting the first layer 31 (the melting point (° C.) of the material constituting the second layer 32/the melting point (° C.) of the material constituting the first layer 31) in one or more embodiments may be 0.98 or less, 0.95 or less, further 0.85 or less, and 0.8 or less. Setting the upper limit of the melting point (° C.) ratio of the material constituting the second layer 32 to the material constituting the first layer 31 to be within the above range can prevent quench distortion and heat shrinkage of the multilayer tube upon production thereof, consequently being able to prevent the multilayer tube from flattening. No limitation is given to the lower limit of the melting point (° C.) ratio of the material constituting the second layer 32 to the material constituting the first layer 31. However, the lower limit may be, for example, 0.3 or more, 0.4 or more, or 0.5 or more.

The melting point of the material constituting the second layer 32 in one or more embodiments may be lower than the material constituting the first layer 31 by 5° C. or more, 10° C. or more lower, further 30° C. or more lower, and 40° C. or more lower. Setting the lower limit of a difference between the melting points of the material constituting the second layer 32 and of the material constituting the first layer 31 to be within the above range can reduce quench distortion and heat shrinkage of the multilayer tube upon production thereof, consequently rendering the multilayer tube unlikely to flatten. No limitation is given to the upper limit of the difference between the melting points of the material constituting the second layer 32 and of the material constituting the first layer 31. However, the upper limit may be, for example, 200° C. or less, 190° C. or less, or 180° C. or less.

When the insertion member 3 and the outer tubular member 4 flatten, such flattening causes friction between an outer surface of the insertion member 3 and an inner surface of the outer tubular member 4 or between an inner surface of the insertion member 3 and a GW. This friction deteriorates slidability. At least one of the insertion member 3 or the outer tubular member 4 is the multilayer tube, and, in this multilayer tube, the first layer 31 and the second layer 32 have the above-described composition. This composition can reduce occurrence of flattening caused by quench distortion of the insertion member 3 and the outer tubular member 4, at least one of which is the multilayer tube, upon production of these members. Consequently, the reduced occurrence of the flattening decreases contact area and then reduces friction between the outer surface of the insertion member 3 and the inner surface of the outer tubular member 4 and between the inner surface of the insertion member 3 and a GW, thus being able to prevent deterioration in slidability.

The insertion member 3 and the outer tubular member 4 which become flat tend to be deformed in a radial direction when pressure is applied to a circumference of at least one of the insertion member 3 or the outer tubular member 4. This tendency leads to increase in friction between the outer surface of the insertion member 3 and the inner surface of the outer tubular member 4 and between the inner surface of the insertion member 3 and a GW, thus causing deterioration in slidability. This tendency is decreased when at least one of the insertion member 3 or the outer tubular member 4 is the multilayer tube that is prevented from flattening. Such a multilayer tube renders a cross-sectional shape of at least one of the insertion member 3 or the outer tubular member 4 unlikely to be deformed in the radial direction by pressure even though a fluid is supplied into the shaft 2. This prevents the increase in friction between the insertion member 3 and the outer tubular member 4 and between the insertion member 3 and a GW, thus being able to prevent deterioration in slidability.

In a cross-section perpendicular to an axial direction of the multilayer tube, a ratio of a cross-sectional area of the second layer 32 to a cross-sectional area of the first layer 31 (a cross-sectional area of the second layer 32/a cross-sectional area of the first layer 31) is 0.7 or less. A combination of such a cross-sectional area ratio of the second layer 32 to the first layer 31 and the above-described the material constituting respectively in the first layer 31 and the material constituting respectively in the second layer 32 prevents at least one of the insertion member 3 or the outer tubular member 4, which is the multilayer tube, from flattening, and reduces friction between the insertion member 3 and the outer tubular member 4 and between the insertion member 3 and a GW, thus being able to improve slidability.

The ratio of the cross-sectional area of the second layer 32 to the cross-sectional area of the first layer 31 (the cross-sectional area of the second layer 32/the cross-sectional area of the first layer 31) merely needs to be 0.7 or less. Especially, the ratio of the cross-sectional area of the second layer 32 to the cross-sectional area of the first layer 31 in one or more embodiments may be 0.55 or less, 0.40 or less, and 0.30 or less. Setting the upper limit of the cross-sectional area ratio of the second layer 32 to the first layer 31 in this manner can effectively prevent at least one of the insertion member 3 or the outer tubular member 4, which is the multilayer tube, from flattening.

In the cross-section perpendicular to the axial direction of the multilayer tube, the multilayer tube has an initial roundness calculated by the equation (1) described below of 92% or more. The initial roundness represents a degree of flattening before use of the catheter 1, that is, before the shaft 2 is pressurized. Higher initial roundness of the multilayer tube can bring about less flattening. Such composition of the multilayer tube reduces the degree of flattening caused by quench distortion of the multilayer tube upon production thereof. The reduced degree of flattening renders the multilayer tube unlikely to be deformed in the radial direction by pressure even though a fluid is supplied into the shaft 2. This prevention can bring about excellent slidability.

In the cross-section perpendicular to the axial direction of the multilayer tube, the initial roundness merely needs to be 92% or more but in one or more embodiments may be 95% or more, 95.5% or more, further 96% or more, and 97% or more. Setting the initial roundness of the multilayer tube to be within the above range reduces the degree of flattening caused by quench distortion of the multilayer tube upon production thereof. The reduced degree of flattening renders the multilayer tube unlikely to be deformed in the radial direction by pressure even though a fluid is supplied into the shaft 2. This prevention can bring about excellent slidability.

In the cross-section perpendicular to the axial direction of the multilayer tube, the initial roundness can be calculated by the following equation (1).

$$\text{initial roundness (\%)} = (\text{a minor axis outer diameter of the multilayer tube/a major axis outer diameter of the multilayer tube}) \times 100 \quad (1)$$

On the proximal side of the shaft 2 may be provided a hub 20 to improve operability. The hub 20 includes a treatment part 22 communicating with a first lumen 5 that is an insertion passage for a GW and includes a fluid injection part 21 communicating with a second lumen 6 that is a flow passage for a fluid such as a pressurized fluid. The treatment part 22 can function as an injection port for a medicament or the like and as a suction port for a fluid or the like in a body lumen, in addition to the function for GW insertion.

To the second lumen 6 may be connected a leak valve. Such structure enables drainage of a fluid that is supplied into the second lumen 6, thus it may be used for safety in one or more embodiments.

To the second lumen 6 may be connected a check valve. Such structure prevents backflow of a fluid that is supplied into the second lumen 6 towards a hand side.

The leak valve and the check valve in one or more embodiments may be provided on the proximal side of the catheter 1. The hub 20 may be provided with a button and a lever to operate the leak valve and the check valve.

To the hub 20 may be connected a syringe for operating supply and drainage of a fluid into and from the second lumen 6. This syringe in one or more embodiments may be a small-diameter syringe for enhancement of operability but not particularly limited thereto.

The insertion member 3, the outer tubular member 4, and the hub 20 can be joined together by a conventionally known joining means such as adhesive and heat welding. Amongst these, in one or more embodiments junction by the heat welding may be used. Such junction can eliminate leakage of a component of an adhesive, thus being able to produce the catheter 1 having high safety.

One or more embodiments of the present disclosure may be applied to a so-called rapid exchange catheter in which a GW is inserted halfway from the proximal side to the distal side. In this case, the insertion passage for a GW may be provided on a part of the insertion member including the distal side of the shaft.

In in one or more embodiments, the shaft 2 may have the second lumen 6 into which a fluid is supplied between the outside of the insertion member 3 and the inside of the outer tubular member 4. The shaft 2 having this structure can enhance rigidity of a distal end thereof owing to a fluid supplied into the second lumen 6, thus being able to improve pushability of the catheter 1. In a case where the shaft 2 has on its distal side a balloon 8 communicating with the second lumen 6, such a fluid supply enables expansion of the balloon 8.

The shaft 2 may at least partly have double-tube structure (coaxial structure); this coaxial structure in one or more embodiments may be on the distal side of the shaft 2. That is, the shaft 2 in one or more embodiments may be provided with the second lumen 6 at least on the distal side thereof. In the coaxial structure, the second lumen 6 entirely encloses a circumference of the shaft 2 so that an entire circumferential direction of the shaft 2 can be pressurized in a balanced manner upon supply of a fluid into the second lumen 6. This balanced pressurization can render flattening of the insertion member 3 and the outer tubular member 4 unlikely to occur. Besides, although passability of a GW in a lesion depends largely upon rigidity of its distal side, the shaft 2 having the second lumen 6 on the distal side thereof in this manner achieves favorable passability of a GW in a lesion.

To produce the shaft 2 having simple structure, the outer tubular member 4 may be provided to enclose the outside of the insertion member 3 in an entire distal and proximal direction thereof. That is, the shaft 2 may have the coaxial structure in the entire distal and proximal direction of the insertion member 3. Alternatively, the shaft 2 may have the coaxial structure on the distal side and have biaxial structure on the proximal side.

Rigidity of the entire shaft 2 may be varied in an axial direction thereof by changing, within a span of the second lumen 6 of the shaft 2, an inner diameter or an outer diameter of the insertion member 3, or an inner diameter or an outer diameter of the outer tubular member 4. Rigidity of the entire shaft 2 can also be varied by changing Shore D hardness of the material constituting the insertion member 3 or the outer tubular member 4 in the axial direction thereof. The Shore D hardness is measured in accordance with ISO868:2003 Testing Methods for Durometer Hardness of Plastics.

Cross-sectional area of the second lumen 6 may be varied in a major axial direction by changing the outer diameter of the insertion member 3 or the inner diameter of the outer tubular member 4. For example, the outer diameter of the insertion member 3 or the inner diameter of the outer tubular member 4 may increase or decrease towards the distal side. This can bring variation to an enhancement rate of rigidity of the shaft 2 in the axial direction upon supply of a fluid into the second lumen 6, thus being able to improve passability of the shaft 2 in a lesion.

The second lumen 6 in one or more embodiments may not be provided on the distal end of the shaft 2. That is, a distal end of the second lumen 6 may be provided more proximally than the distal end of the shaft 2 in one or more embodiments. Specifically, the distal end of the second lumen 6 may be provided on a position that is 1 mm or more proximal to the distal end of the shaft 2 in one or more embodiments. This position in one or more embodiments may be 3 mm or more, and further 5 mm or more proximal to the distal end of the shaft 2. Such a position can prevent rigidity of the distal end of the shaft 2 from being excessively enhanced, thus being able to prevent the distal end from hurting a region other than a lesion owing to inadvertent contact.

On the other hand, the distal end of the second lumen 6 that is excessively close to the proximal side might deteriorate pushability of a GW on the distal side. Hence, the distal end of the second lumen 6 in one or more embodiments may be on a position that is 35 mm or less proximal to the distal end of the shaft 2. This position may be 30 mm or less proximal to the distal end of the shaft 2 in one or more embodiments.

As shown in FIG. 6, the shaft 2 may have a third lumen 7 into which a fluid is supplied in one or more embodiments. The shaft 2 having this structure can much improve pushability of the shaft 2. In one or more embodiments, the catheter 1 may further include on the distal side of the shaft 2 a balloon 8 connected to the third lumen 7. The catheter 1 having this structure achieves excellent pushability and enables efficient expansion of a stenosed part of a blood vessel.

In one or more embodiments, the outer tubular member 4 and the insertion member 3 may be relatively movable in the distal and proximal direction. This means that the insertion member 3 can be, without any resistance, inserted into and also slid in a lumen of the outer tubular member 4. The outer tubular member 4 and the insertion member 3 that have such structure enable delivery of the insertion member 3, which has a smaller diameter than that of the outer tubular member 4, into a desired region in a body. The delivery of the insertion member 3 thereafter enables the outer tubular member 4 to easily reach, along the insertion member 3, the desired region.

The insertion member 3 and the outer tubular member 4 may be joined together at a distal end part of the shaft 2. This joint suitably enhances rigidity of the distal end part of the shaft 2, thus being able to improve pushability. For example, in FIG. 3, the insertion member 3 and the outer tubular member 4 are joined at the distal end part of the shaft 2 including the distal end of the shaft 2. In FIG. 4, the insertion member 3 and the outer tubular member 4 are joined more proximally than the distal end of the shaft 2. Such a joint of the insertion member 3 and the outer tubular member 4 can prevent rigidity of the distal end of the shaft 2 from being excessively enhanced, thus being able to prevent the distal end of the shaft 2 from hurting a region other than a lesion owing to inadvertent contact.

At a joint part of the insertion member 3 and the outer tubular member 4, rigidity may be varied gradually in one or more embodiments. Such variation in rigidity can enhance kink resistance of the shaft 2. Examples of structure that can gradually vary rigidity of the shaft 2 in the axial direction include one having the joint part at which the outer diameter of the outer tubular member 4 gradually increases towards the proximal side.

The insertion member 3 and the outer tubular member 4, though not illustrated, may partly be joined together on a position on which the second lumen 6 is provided, to a degree that does not impede fluid communication in the lumen. Partly joining the insertion member 3 and the outer tubular member 4 together can enhance coaxiality of the insertion member 3 and the outer tubular member 4 when the shaft 2 is pushed towards the axial direction upon treatment.

The shaft 2, though not illustrated, may have an end tip member at its distal end part. Providing the end tip member can prevent the distal end of the shaft 2 from hurting a region other than a lesion owing to inadvertent contact. In one or more embodiments, the end tip member may be joined to either the insertion member 3 or the outer tubular member 4 but may be joined to the outer tubular member 4 to allow gradual transition of flexibility of the shaft 2 in the axial direction.

In one or more embodiments, the end tip member may have lower Shore D hardness than that of at least one of the insertion member 3 or the outer tubular member 4. Such an end tip member can prevent the distal end part of the shaft 2 from hurting a region other than a lesion owing to inadvertent contact.

In one or more embodiments, the shaft 2 may have a radiopaque marker disposed on its distal side. Specifically, in one or more embodiments the radiopaque marker may be provided on a distal side of the insertion member 3. In one or more embodiments, the radiopaque marker may be provided on a position that is 0 mm or more and 30 mm or less proximal to the distal end of the second lumen 6, and may further be provided on a position that is 0 mm or more and 5 mm or less proximal to the distal end of the second lumen 6. This renders it possible to check into where the shaft 2 is inserted. For the radiopaque marker, a conventionally known marker may be used. A radiopaque substance for the radiopaque marker may be, for example, lead, barium, iodine, tungsten, gold, platinum, iridium, stainless steel, titanium, a cobalt chromium alloy or the like.

In one or more embodiments, in a case where the catheter 1 includes the balloon 8 on its distal side, the catheter 1 may be provided with one or more radiopaque markers in a vicinity of the balloon 8. This renders it possible to check where the balloon 8 is.

The outer tubular member 4 may have a single layer or multiple layers in which the single layers are laminated. That is, the outer tubular member 4 may be the multilayer tube having the first layer 31 and the second layer 32. Examples of a method for producing the outer tubular member 4 having the first layer 31 and the second layer 32 include: a method of co-extrusion molding in which the material for the first layer 31 and the material for the second layer 32 are simultaneously extruded; and a method in which the first layer 31 is formed by, for example, coating one surface of an already prepared tubular member that is to be the second layer 32. Amongst these, in one or more embodiments the method for producing by co-extrusion molding the outer tubular member 4 having the first layer 31 and the second layer 32 may be used. Such a method can produce the outer tubular member 4 in which the first layer 31 and the second layer 32 respectively have uniform thicknesses.

In a case where the outer tubular member 4 is the multilayer tube having the first layer 31 and the second layer 32, the second layer 32 may be disposed to become the innermost layer of the outer tubular member 4 in one or more embodiments. The outer tubular member 4 having this structure can improve slidability between the outer tubular member 4 and the insertion member 3.

The outer tubular member 4 may be, for example, a resin tube extruded by extrusion molding. Examples of a resin forming the outer tubular member 4 include polyamide-based resin, polyester-based resin, polyurethane-based resin, polyolefin-based resin, fluorine-based resin, vinyl chloride-based resin, silicone-based resin and natural rubber. These may be used alone or in combination of two or more kinds. Amongst these, the polyamide-based resin, the polyester-based resin, the polyurethane-based resin, the polyolefin-based resin and the fluorine-based resin may be used in one or more embodiments.

Rigidity of the outer tubular member 4 may be enhanced by adjusting thickness of the outer tubular member 4. The outer tubular member 4 according to one or more embodiments of the present disclosure may have the thickness of 0.02 mm or more, and 0.06 mm or more. In addition, to prevent the outer diameter of the outer tubular member 4 from becoming excessively large, the outer tubular member 4 in one or more embodiments may have the thickness of 1.00 mm or less, 0.50 mm or less, and further 0.30 mm or less.

The insertion member 3 may be the same tubular shape as that of the outer tubular member 4, or be a solid column shape. The insertion member 3 of the tubular shape can have the first lumen 5 inside in the radial direction, and into this first lumen 5 can be inserted or supplied a GW or a fluid. The insertion member 3 of the column shape can impart to itself a function of a OW. Examples of a cross-sectional shape of the insertion member 3 of the column shape include a circular shape, an oval shape and a polygonal shape. Amongst these, the circular shape to improve slidability with the outer tubular member 4 may be used in one or more embodiments.

The insertion member 3 may have a single layer or multiple layers in which the single layers are laminated. Amongst these, the insertion member 3 in one or more embodiments may be the multilayer tube having the first layer 31 and the second layer 32. The insertion member 3 having this structure can reduce contact areas between the outer surface of the insertion member 3 and the inner surface of the outer tubular member 4, and between the inner surface of the insertion member 3 and a GW and can reduce friction there between, thus being able to prevent deterioration in slidability. In addition, such structure renders the insertion member 3 unlikely to flatten and thus can achieve excellent slidability even though the insertion member 3 is pressurized by a fluid supplied into the shaft 2. A method for producing the insertion member 3 having the first layer 31 and the second layer 32 may be the above-exemplified method for producing the outer tubular member 4 having the first layer 31 and the second layer 32. Besides, both the insertion member 3 and the outer tubular member 4 in one or more embodiments may be the multilayer tubes. The insertion member 3 and the outer tubular member 4 that are structured in this manner render both the insertion member 3 and the outer tubular member 4 unlikely to flatten, thus being able to improve slidability between the insertion member 3 and the outer tubular member 4.

In a case where the insertion member 3 is the multilayer tube having the first layer 31 and the second layer 32, the second layer 32 in one or more embodiments may be disposed to become the innermost layer of the insertion member 3. The insertion member 3 having this structure can improve slidability between a GW and the insertion member 3. In one or more embodiments, it may be provided that the second layer 32 is disposed to become the outermost layer of the insertion member 3. The insertion member 3 having such structure can improve slidability between the outer tubular member 4 and the insertion member 3.

In one or more embodiments, the insertion member 3 may have the first lumen 5 into which a guide wire is inserted. The insertion member 3 having this structure enables insertion of a GW into the lumen of the insertion member 3, thus enabling the catheter 1 to easily reach an intended region such as a lesion.

The insertion member 3 may be, for example, a resin tube or a columnar resin member that is extruded by extrusion molding. A resin forming the insertion member 3 may be the resin exemplified as one forming the outer tubular member 4.

In a case where the insertion member 3 is the tubular shape, rigidity of the insertion member 3 may be enhanced by adjusting thickness of the insertion member 3. Conventionally, upon applying a pressure (for example, 14 to 30 atm), which is commonly necessary for expansion of a balloon, to an outer surface of a resin tube used as a shaft of a balloon catheter, such a pressure deforms the tube in a radial direction. As a result of the deformation, an inner surface of the tube comes into contact with a common GW having an outer diameter of approximately 0.356 mm to 0.39 mm, thus rendering the GW unlikely to slide in a distal and proximal direction along the tube in some cases. Hence, the insertion member 3 according to one or more embodiments of the present disclosure may have a thickness of 0.03 mm or more, and 0.05 mm or more. In addition, the insertion member 3 in one or more embodiments may have the thickness of 0.20 mm or less, 0.16 mm or less, and further 0.12 mm or less to prevent the outer diameter of the insertion member 3 from becoming excessively large.

In a case where the insertion member 3 is the tubular shape, a ratio of a Shore D hardness of the material constituting the outer tubular member 4 to a Shore hardness of the material constituting the insertion member 3 in one or more embodiments may be 0.9 or more, 1.0 or more, and further 1.2 or more from a perspective of preventing the first lumen 5 from being deformed in the radial direction by pressure.

In one or more embodiments, the insertion member 3 may have high rigidity in order for its outer diameter not to be varied easily even though expansion pressure is increased to predetermined pressure or more. The high rigidity renders the insertion member 3 and the first lumen 5 into which a GW is inserted unlikely to be deformed in the radial direction by pressure even though a fluid is supplied into the second lumen 6. Consequently, this high rigidity can prevent deterioration in slidability.

In one or more embodiments, the insertion member 3 may have high uniformity between its inner and outer diameters in the radial direction in a cross-section perpendicular to the axial direction of the insertion member 3. That is, in the cross-section perpendicular to the axial direction of the insertion member 3, a difference of thickness in the first layer 31 and a difference of thickness in the second layer 32 in the radial direction of the insertion member 3 in one or more embodiments may be small.

Specifically in one or more embodiments, the maximum thickness in the first layer 31 in the radial direction of the insertion member 3 may be 1.20 times or less, 1.10 times or less, and 1.05 times or less as large as the minimum thickness in the first layer 31 in the cross-section perpendicular to the axial direction of the insertion member 3. The insertion member 3 having in the radial direction such a thickness in the first layer 31 can enhance uniformity between inner and outer diameters of the first layer 31.

In addition, the maximum thickness in the second layer 32 in the radial direction of the insertion member 3 in one or more embodiments may be 1.20 times or less, 1.10 times or less, and further 1.05 times or less as large as the minimum thickness in the second layer 32 in the cross-section perpendicular to the axial direction of the insertion member 3. The insertion member 3 having in the radial direction such a thickness in the second layer 32 can enhance uniformity between inner and outer diameters of the second layer 32. At least one of the first layer 31 or the second layer 32 having enhanced uniformity between its inner and outer diameters can enhance uniformity between the inner and outer diameters of the insertion member 3 in the radial direction.

A thickness ratio of the second layer 32 to the first layer 31 (the thickness of the second layer 32/the thickness of the first layer 31) in the radial direction of the insertion member 3 in one or more embodiments may be 0.20 or more, 0.22 or more, and further 0.25 or more in the cross-section perpendicular to the axial direction of the insertion member 3. Setting the lower limit of the thickness ratio of the second layer 32 to the first layer 31 in this manner enables stable formation of the second layer 32 without breakage. In addition, the thickness ratio of the second layer 32 to the first layer 31 (the thickness of the second layer 32/the thickness of the first layer 31) in the radial direction of the insertion member 3 in one or more embodiments may be 0.60 or less, 0.50 or less, further 0.40 or less, and 0.35 or less in the cross-section perpendicular to the axial direction of the insertion member 3. Setting the upper limit of the thickness ratio of the second layer 32 to the first layer 31 in this manner can reduce flattening occurrence of the insertion member 3 caused by quench distortion upon production of the insertion member 3 and can simultaneously enhance uniformity between the inner and outer diameters of the insertion member 3 in the radial direction.

In one or more embodiments, the insertion member 3 may have a roundness after pressure test, which is calculated by the following equation (2) after pressure test, of 75% or more in the cross-section perpendicular to the axial direction of the insertion member 3. The roundness after pressure test represents a degree of flattening of the insertion member 3 after use of the catheter 1, and the use of the catheter 1 is simulated by pressure test in which the second lumen 6 is repeatedly pressurized.

The pressure test is performed by the following steps.

(i) disposing a core material within the first lumen 5, (ii) placing the catheter 1 under a 1 atm (atmospheric pressure) and 37° C. water environment, (iii) applying pressure of rated burst pressure (RBP)+1 atm (atmospheric pressure) to within the second lumen 6 for 30 seconds, (iv) depressurizing the pressure within the second lumen 6 to 1 atm (atmospheric pressure), and (v) repeating the above (iii) to (iv) 20 times In the step (i), the core material may be a GW or be a core material of stainless steel, a nickel alloy, a titanium alloy, or the like that resembles a GW. Amongst these, in one or more embodiments the stainless steel core material may have easy handleability.

In the step (ii), to perform the pressure test in an approximation of practical usage of the catheter 1, a pressurized medium is 37° C. water. The pressurized medium may be a fluid of another kind. Examples of the pressurized medium include a liquid such as saline, and a gas such as air and a nitrogen gas. A temperature of the pressurized medium may optionally be higher or lower than 37° C., or the like to perform the test simulating a severe environment.

In the step (iii), the pressure, which is the rated burst pressure (RBP) of the catheter 1 plus 1 atm of atmospheric pressure, is applied to within the second lumen 6 for 30 seconds. This pressure applies a load that deforms the insertion member 3 in the radial direction. The RBP is the maximum balloon inflation pressure of a balloon catheter that can be statistically guaranteed. Besides, 1 atm is 1013 hPa.

In the step (iv), the pressure within the second lumen 6 is depressurized to 1 atm (atmospheric pressure). In the step (v), the step (iii) and the step (iv) are repeated 20 times in total. This step (v) enables confirmation of a degree to which the insertion member 3 flattens when a fluid is repeatedly supplied into the second lumen 6.

The roundness after pressure test of the insertion member 3 can be calculated by the following equation (2).

$$\text{roundness after pressure test (\%)} = (\text{an outer diameter of the insertion member 3 after the pressure test at the point of the minor axis outer diameter thereof upon the calculation of the initial roundness/an outer diameter of the insertion member 3 after the pressure test at the point of the major axis outer diameter thereof upon the calculation of the initial roundness}) \times 100 \quad (2)$$

That is, a minor axis outer diameter and a major axis outer diameter are measured after the pressure test at the point where the minor axis outer diameter and the major axis outer diameter of the insertion member 3 are measured upon the calculation of the initial roundness. The measured values are assigned to the above equation (2) to determine the roundness after pressure test. The insertion member 3 having a higher roundness after pressure test can ostensibly cause less flattening of the shaft 2 after pressurization.

In one or more embodiments, the insertion member 3 may be the roundness after pressure test of 75% or more in the cross-section perpendicular to the axial direction of the insertion member 3. In one or more embodiments, the roundness after pressure test may be 80% or more, 85% or more, and further 90% or more. Setting the roundness after pressure test of the insertion member 3 to be within the above range reduces deformation of the insertion member 3 in the radial direction after repeated supply of a fluid into the second lumen 6, thus enabling excellent slidability of the insertion member 3.

When a fluid is supplied with the RBP into the second lumen 6, an outer diameter reduction rate of the insertion member 3 at a point where the outer diameter of the insertion member 3 becomes smallest in one or more embodiments may be within 10%. The outer diameter reduction rate in one or more embodiments may be within 8%, and further within 6%. Setting the outer diameter reduction rate of the insertion member at the point where the outer diameter of the insertion member 3 becomes smallest to be within the above range renders the first lumen 5 into which a GW is inserted unlikely to be deformed in the radial direction by pressure even though a fluid is supplied into the second lumen 6. Consequently, deterioration in slidability of a GW can be prevented.

In one or more embodiments, the point where the outer diameter of the insertion member 3 becomes smallest may be inside the second lumen 6. This renders the first lumen 5 into which a GW is inserted unlikely to be deformed in the radial direction by pressure even though a fluid is supplied into the second lumen 6. Consequently, deterioration in slidability of a GW can be prevented.

In one or more embodiments, the point where the outer diameter of the insertion member 3 becomes smallest may be on the distal side of the shaft 2. In one or more embodiments, the point may be on a position that is 0 cm or more and 100 cm or less, and further 0 cm or more and 60 cm or less proximal to the distal end of the shaft 2. This enhances rigidity of the distal side of the shaft 2, thus improving passability of a GW in a lesion.

Specific examples of the material constituting the first layer 31 include: a polyamide-based resin such as nylon 12, a nylon 12 elastomer, nylon 6 and aromatic polyamide; a polyimide-based resin; a polyurethane-based resin such as thermoplastic polyurethane; a crystalline thermoplastic resin such as a polyetheretherketone resin and a fluorine-based resin such as polyvinylidene fluoride and polyvinyl fluoride; an amorphous thermoplastic resin such as a polystyrene resin, polyvinyl chloride and an acrylic resin; a thermosetting resin such as a silicone-based resin; and natural rubber. These may be used alone or in combination of two or more kinds. Amongst these, in one or more embodiments the thermoplastic resin may have easy handleability. In one or more embodiments, polyamide-based resin may be used, and in further embodiments the nylon 12 and the nylon 12 elastomer may be used. Owing to such at least one material included in the first layer 31, the first layer 31 has a high melting point and a low crystallinity degree. This reduces occurrence of quench distortion of the first layer 31, thus being able to prevent its slidability from deteriorating.

Specific examples of the material constituting the second layer 32 include: a non-polar polyolefin-based resin such as polyethylene and polypropylene; a polyamide-based resin such as nylon 12, a nylon 12 elastomer, nylon 6 and aromatic polyamide; a polyester-based resin such as a polyetheretherketone resin and polyethylene terephthalate; a thermoplastic resin such as a fluororesin such as polytetrafluoroethylene; a silicone-based resin; and natural rubber. These may be used alone or in combination of two or more kinds. Amongst these, in one or more embodiments the thermoplastic resin may have easy handleability. In one or more embodiments, the non-polar polyolefin-based resin may be used. Further, in one or more embodiments a polyethylene-based resin such as high-density polyethylene, medium-density polyethylene and low-density polyethylene, and high-density polyethylene and low-density polyethylene may be used. Owing to such at least one material included in the second layer 32, a surface of the second layer 32 becomes slippery, thus being able to much improve its slidability. A classification of the polyethylene such as the high-density polyethylene and the low-density polyethylene is based upon JIS K6922-1 that defines polyethylene having a density of 910 kg/m3 or more and less than 930 kg/m3 as the low-density polyethylene; polyethylene having a density of 930 kg/m3 or more and less than 942 kg/m3 as the medium-density polyethylene; and polyethylene having a density of 942 kg/m3 or more as the high-density polyethylene.

In one or more embodiments, the material constituting the first layer 31 and the material constituting the second layer 32 may be a thermoplastic resin. Such materials constituting the first layer 31 and the second layer 32 facilitate lamination of the first layer 31 and the second layer 32 and also strengthen the lamination of the first layer 31 and the second layer 32.

In one or more embodiments, the second layer 32 may be disposed more inside in the radial direction than the first layer 31. The second layer 32 having this structure prevents the multilayer tube from flattening and can improve slidability with a GW and the insertion member 3 that are disposed inside the multilayer tube in the radial direction. Inversely, the second layer 32 in one or more embodiments may also be disposed more outside in the radial direction than the first layer 31. The second layer 32 having this structure renders the multilayer tube unlikely to be deformed by pressure when the pressure is applied to the multilayer tube from its outside in the radial direction.

A ratio of a Shore D hardness of the material constituting the first layer 31 to a Shore D hardness of the material constituting the second layer 32 (a Shore D hardness of the material constituting the first layer 31/a Shore D hardness of the material constituting the second layer 32) in one or more embodiments may be 0.9 or more. In one or more embodiments, the Shore D hardness ratio may be 1.0 or more, and further 1.1 or more. Setting the lower limit of the ratio of the Shore D hardness of the material constituting the first layer 31 to the Shore D hardness of the material constituting the second layer 32 in this manner can prevent the multilayer tube from being deformed by pressure and then from causing deterioration in its slidability when the pressure is applied to the multilayer tube. The upper limit of the ratio of the Shore D hardness of the material constituting the first layer 31 to the Shore D hardness of the material constituting the second layer 32 is not limited but is, for example, it may be 3.0 or less, 2.5 or less, and further 2.0 or less in one or more embodiments. Setting the upper limit of the ratio of the Shore D hardness of the material constituting the first layer 31 to the Shore D hardness of the material constituting the second layer 32 in this manner imparts moderate flexibility to the multilayer tube, thus achieving the catheter 1 that easily passes a stenosed part of a blood vessel.

The second layer 32 may have a layer A 33 and a layer B 34 laminated with the layer A 33. For example, as shown in FIG. 2, the insertion member 3 has the first layer 31 and the second layer 32, and the second layer 32 may have the layer A 33 and the layer B 34. As shown in FIG. 7, the outer tubular member 4 has the first layer 31 and the second layer 32, and the second layer 32 may have the layer A 33 and the layer B 34. That is, at least one of the insertion member 3 or the outer tubular member 4 has, from its outside in the radial direction, three layers that are the first layer 31, the layer B 34 and the layer A 33, or that are the layer A 33, the layer B 34 and the first layer 31, and the layer B 34 may join the first layer 31 and the layer A 33. In the radial direction, the first layer 31 is one side of at least one of the insertion member 3 or the outer tubular member 4, and the layer A 33 is another side of the insertion member 3. This structure can join the first layer 31 and the layer A 33 via the layer B 34 even though the at least one material included in the first layer 31 and a material forming the layer A 33 are difficult to be joined. Specifically, the layer B 34 is formed from a material that can be joined to both the at least one material included in the first layer 31 and the material forming the layer A 33. Disposing such a layer B 34 between the first layer 31 and the layer A 33 enables junction of the first layer 31a and the layer A 33.

Examples of a method for producing the second layer 32 having the layer A 33 and the layer B 34 include a method of co-extrusion molding in which the respective materials for the first layer 31, the layer A 33 and the layer B 34 are simultaneously extruded; and a method in which the layer B 34 is formed by, for example, coating the outside of an already prepared tubular member that is to be the layer A 33, and then the first layer 31 is formed by, for example, coating the outside of the layer B 34. Amongst these, the method for producing by co-extrusion molding the multilayer tube having the first layer 31 and the second layer 32 having the layer A 33 and the layer B 34 may be used in one or more embodiments. Such a method can produce the first layer 31, the layer A 33 and the layer B 34 that respectively have uniform thicknesses.

In one or more embodiments, the material constituting the layer A 33 may have a higher Shore D hardness than that of the material constituting the layer B 34. The layer A 33 constitutes one side of the multilayer tube in the radial direction, and thus this side of the multilayer tube can have high firmness. This high firmness can prevent the multilayer tube from being deformed in the radial direction by pressure when a fluid is supplied into the second lumen 6. In one or more embodiments, the Shore D hardness of the material constituting the layer A 33 may have 1.2 times or more, 1.3 times or more, and further 1.4 times or more as high as a Shore D hardness of the material constituting the layer B 34. Setting the Shore D hardness of the material constituting the layer A 33 to be within the above range can increase firmness of the one side of the multilayer tube. This increased firmness can prevent the multilayer tube from being deformed by pressure when a fluid is supplied into the second lumen 6.

In one or more embodiments, the Shore D hardness of the material constituting the layer A 33 may be 1.0 time or more, 1.1 times or more, and further 1.2 times or more as high as the Shore D hardness of the material constituting the first layer 31. Setting the Shore D hardness of the material constituting the layer A 33 to be within the above range can increase firmness of the one side of the multilayer tube. This increased firmness can prevent the multilayer tube from being deformed in the radial direction by pressure when a fluid is supplied into the second lumen 6.

Specific examples of the material constituting the layer A 33 include a polyolefin-based resin such as polyethylene and polypropylene; a polyester-based resin such as polyethylene terephthalate; and a fluorine-based resin such as polytetrafluoroethylene. Amongst these, in one or more embodiments a polyethylene-based resin may have a slippery surface. In one or more embodiments, a non-adhesive polyethylene resin, and further a non-adhesive high-density polyethylene resin may be used. This can improve slidability of the multilayer tube. Further, by increasing firmness of the layer A 33, the multilayer tube can be prevent from being deformed in the radial direction by pressure.

Specific examples of the material constituting the layer B 34 include a polyethylene-based resin such as low-density polyethylene and linear low-density polyethylene. Amongst these, an adhesive polyethylene resin, and an adhesive linear low-density polyethylene resin may be used in one or more embodiments. This enables firm junction of the layer A 33 and the first layer via the layer B 34.

In one or more embodiments, to enhance uniformity between inner and outer diameters of the second layer 32, a difference of thickness in the layer A 33 and a difference of thickness in the layer B 34 in the radial direction of the multilayer tube may be small in the cross-section perpendicular to the axial direction of the multilayer tube. Specifically, the maximum thickness in the layer A 33 in the radial direction of the multilayer tube in one or more embodiments may be 1.20 times or less, 1.10 times or less, and further 1.05 times or less as large as the minimum thickness in the layer A 33 in the cross-section perpendicular to the axial direction of the multilayer tube. The layer A 33 having such a thickness in the radial direction of the multilayer tube can enhance uniformity between its inner and outer diameters.

In addition, the maximum thickness in the layer B 34 in the radial direction of the multilayer tube in one or more embodiments may be 1.20 times or less, 1.10 times or less, and further 1.05 times or less as large as the minimum thickness in the layer B 34. The layer B 34 having such a thickness in the radial direction of the multilayer tube can enhance uniformity between its inner and outer diameters. Enhancing uniformity between the inner and outer diameters of at least one of the layer A 33 or the layer B 34 enhances uniformity between the inner and outer diameters of the second layer. This enhanced uniformity can consequently enhance inner and outer diameters of the multilayer tube in the radial direction.

In one or more embodiments, the multilayer tube may have in the radial direction a thickness ratio of the layer B 34 to the layer A 33 (the thickness of the layer B 34/the thickness of the layer A 33) of 0.1 or more, 0.3 or more, and further 0.5 or more in the cross-section perpendicular to the axial direction of the multilayer tube. Setting the lower limit of the thickness ratio of the layer B 34 to the layer A 33 in this manner enables the layer B 34 to sufficiently join the layer A 33 and the first layer. In addition, in one or more embodiments the multilayer tube may have in the radial direction the thickness ratio of the layer B 34 to the layer A 33 (the thickness of the layer B 34/the thickness of the layer A 33) of 1.2 or less, 1.1 or less, and further 1.0 or less. Setting the upper limit of the thickness ratio of the layer B 34 to the layer A 33 in this manner leads to sufficient firmness of the layer A 33.

As shown in FIG. 5, the catheter 1 in one or more embodiments may include the balloon 8 connected on a distal side of the second lumen 6. The catheter 1 including the balloon 8 can efficiently expand a stenosed part of a blood vessel. Expanding the balloon 8 in a normal blood vessel before (proximal to) a stenosed part or in a concomitantly used guiding catheter prevents an unexpected shift in position of the catheter 1 in its major axial direction upon operation of a GW. This prevention can further enhance capability of a GW as a backup.

A material constituting the balloon 8 may be, for example, the material that forms the first layer 31 but is not particularly limited thereto.

The balloon 8 can be produced to have the same size, shape or the like as that of a balloon of a known balloon catheter. As a method for producing the balloon 8, a production method of a known balloon can be adopted. The balloon 8 may be provided with a reinforcement, a scoring member, cutting member, a medicament layer or a hydrophilic coating layer.

At least one of the insertion member 3 or the outer tubular member 4 in one or more embodiments may include a stiffener to enhance rigidity of the insertion member 3 and the outer tubular member 4. FIG. 8 is a cross-sectional view showing an example of the insertion member 3 provided with the stiffeners. As shown in FIG. 8, the stiffener 10 may be, for example, a wire provided inside at least one of the insertion member 3 or the outer tubular member 4 in one or more embodiments. In a case where the stiffener 10 is the wire, at least part of the wire may be embedded in a wall of at least one of the insertion member 3 and the outer tubular member 4 in one or more embodiments. The stiffener 10 provided in this manner can sufficiently enhance rigidity of the insertion member 3 and the outer tubular member 4.

The wire used as the stiffener 10 may be, for example, a single metal wire or a twisted metal wire of stainless steel, titanium, a cobalt-chrome alloy or the like. The wire may also be a fiber material, such as a polyarylate fiber, an aramid fiber, an ultrahigh molecular weight polyethylene fiber, a PBO fiber and a carbon fiber. The fiber material may be a monofilament or a multifilament. In one or more embodiments, the wire has higher elasticity than that of the insertion member 3 from a perspective of achieving high firmness of the insertion member 3. For the same reason, the stiffener 10 in one or more embodiments may have higher Shore hardness than that of the insertion member 3.

The stiffener 10 may be one or more spirally arranged wires or a combination of these along an axial direction inside the insertion member 3 and the outer tubular member 4. The stiffener 10 in one or more embodiments may have the wires that are bundled without being woven or the wires that are plaited to further enhance rigidity of the stiffener 10. Amongst these, the plaited wires may be used in one or more embodiments.

The stiffener 10 may contain a radiopaque substance to render it possible under roentgenoscopy to check where the insertion member 3 and the outer tubular member 4 are. The radiopaque substance may be the above-described material. Such a radiopaque substance enables the stiffener 10 to function as a radiopaque marker.

A method for producing the catheter according to one or more embodiments of the present disclosure includes a step of producing by co-extrusion molding the multilayer tube having the first layer 31 and the second layer 32 laminated with the first layer 31.

Specifically, the multilayer tube may be produced by coextruding the at least one material for the first layer 31 and the at least one material for the second layer 32 simultaneously in one or more embodiments. Producing the multilayer tube in this manner can lead to uniform thicknesses of both the first layer 31 and the second layer 32, thus further facilitating firm junction of the first layer 31 and the second layer 32.

This application claims the benefit of the priority date of Japanese patent application No. 2017-251953 filed on Dec. 27, 2017. All of the contents of the Japanese patent application No. 2017-251953 filed on Dec. 27, 2017, are incorporated by reference herein.

EXAMPLES

One or more embodiments of the present disclosure will be specifically explained below based on the following Examples, however, one or more embodiments of the present disclosure is not restricted by the Examples described below of course, and can be certainly put into practice after appropriate modifications within a range meeting the gist of the above and the below, all of which are included in the technical scope of one or more embodiments of the present disclosure.

(Measurement of Roundness 1)

Described below are the measurement results of an initial roundness and a roundness after pressure test of a catheter 1, such as one in FIG. 3, in which a second lumen 6 was provided on a distal side of a shaft 2 and a distal end of the second lumen 6 was proximal to a distal end of the shaft 2. The measurement was performed with an insertion member and an outer tubular member that were respectively prepared. Firstly prepared by co-extrusion was the insertion member of a tubular shape that had a first layer and a second layer having a layer A and a layer B. These layers constituted three-layer structure in which the first layer, the layer B and the layer A were arranged in order from the outside in a radial direction. The prepared insertion member was subjected to an annealing treatment at 80° C. for 1 hour. The first layer was nylon 12 (Nylon 12, Rilsamid (registered trademark) AESNO MED; Arkema, melting point: 169° C., crystallinity degree: 20%, and Shore D hardness: 74). The layer B was linear low-density polyethylene (LLDPE, Plexar (registered trademark) PX3080; Equistar Chemical, melting point: 127° C., and crystallinity degree: 40%). The layer A was high-density polyethylene (HDPE, Novatec (registered trademark) HB530; Japan Polyethylene Corporation, melting point: 136° C., crystallinity degree: 75%, and Shore D hardness: 71). The prepared insertion member had an outer diameter of 0.65 mm and an inner diameter of 0.45 mm. From outer diameters and thicknesses of the first layer and the second layer were respectively determined cross-sectional areas of the first layer and the second layer, and from these cross-sectional areas was calculated a cross-sectional area ratio of the second layer to the first layer. In addition, a minor axis outer diameter and a major axis outer diameter of the insertion member were measured, and from these measured diameters was calculated the initial roundness.

The outer tubular member was prepared by extrusion molding with nylon 12 (Nylon 12, Rilsamid (registered trademark) AESNO MED; Arkema, melting point: 169° C., crystallinity degree: 20%, and Shore D hardness: 74). The prepared outer tubular member had an outer diameter of 1.50 mm and an inner diameter of 1.00 mm.

The outer tubular member is disposed outside the insertion member in the radial direction, and a pressure test was performed by the following steps.

(i) disposing a core material within a first lumen 5, (ii) placing the catheter 1 under a 1 atm (atmospheric pressure) and 37° C. water environment, (iii) applying pressure of rated burst pressure (RBP)+1 atm (atmospheric pressure) to the inside of a second lumen 6 for 30 seconds, (iv) depressurizing the inside of the second lumen 6 to 1 atm (atmospheric pressure), and (v) repeating the above (iii) to (iv) 20 times The RBP was 30 atm. Hence, in the step (iii) of this test, the applied pressure was 31 atm of absolute pressure. The core material was a φ0.36 mm stainless steel core material resembling a GW. After the pressure test, a major axis outer diameter and a minor axis outer diameter of the insertion member were measured, and from the measured diameters was calculated the roundness after pressure test. This measurement was performed at the same point where the minor axis outer diameter and the major axis outer diameter of the insertion member had been measured upon the calculation of the initial roundness.

The composition, the initial roundness and the roundness after pressure test of the insertion member are shown in Table 1.

TABLE 1

| | | | Example 1 | Example 2 | Comparative Example 1 | Comparative Example 2 |
|---|---|---|---|---|---|---|
| Composition | First Layer | Material | Nylon 12 | Nylon 12 | Nylon 12 | Nylon 12 |
| | | Melting Point (° C.) | 169 | 169 | 169 | 169 |
| | | Crystallinity Degree (%) | 20 | 20 | 20 | 20 |
| | | Shore D Hardness | 74 | 74 | 74 | 74 |
| | | Thickness (μm) | 80 | 70 | 50 | 100 |
| | | Cross-sectional Area (mm$^2$) | 0.143 | 0.127 | 0.094 | 0.173 |
| | Second Layer | Layer B Material | LLDPE | LLDPE | LLDPE | — |
| | | Melting Point (° C.) | 127 | 127 | 127 | — |
| | | Crystallinity Degree (%) | 40 | 40 | 40 | — |
| | | Shore D Hardness | — | — | — | — |
| | | Thickness (μm) | 10 | 10 | 10 | — |
| | | Layer A Material | HDPE | HDPE | HDPE | — |
| | | Melting Point (° C.) | 136 | 136 | 136 | — |
| | | Crystallinity Degree (%) | 75 | 75 | 75 | — |
| | | Shore D Hardness | 71 | 71 | 71 | — |
| | | Thickness (μm) | 10 | 20 | 40 | — |
| | | Cross-sectional Area (mm$^2$) | 0.030 | 0.045 | 0.079 | — |
| | | Cross-sectional Area Ratio of Second Layer to First Layer | 0.206 | 0.355 | 0.833 | — |
| Initial State | | Major Axis Outer Diameter (mm) | 0.658 | 0.665 | 0.669 | 0.654 |
| | | Minor Axis Outer Diameter (mm) | 0.643 | 0.634 | 0.632 | 0.645 |
| | | Initial Roundness (%) | 97.7 | 95.3 | 94.5 | 98.6 |
| After Pressure Test | | Major Axis Outer Diameter (mm) | 0.674 | 0.682 | 0.761 | 0.658 |
| | | Minor Axis Outer Diameter (mm) | 0.626 | 0.618 | 0.538 | 0.642 |
| | | Roundness After Pressure Test (%) | 92.9 | 90.6 | 70.7 | 97.6 |

Example 1

Example 1 employed an insertion member in which thicknesses of a first layer, a layer B and a layer A were 80 μm, 10 μm and 10 μm respectively. A catheter in Example 1 had a smaller cross-sectional area ratio of a second layer to the first layer than that of a catheter in Comparative Example 1. The insertion member of the catheter in Example 1 had both a high initial roundness and a high roundness after pressure test.

Example 2

Example 2 employed an insertion member in which thicknesses of a first layer and a layer A were 70 μm and 20 μm respectively. A catheter in Example 2 had also a smaller cross-sectional area ratio of a second layer to the first layer than that of a catheter in Comparative Example 1. The insertion member of the catheter in Example 2 had a high initial roundness and a high roundness after pressure test.

Comparative Example 1

Comparative Example 1 employed an insertion member in which thicknesses of a first layer and a layer A were 50 μm and 40 μm respectively. This first layer was thinner than those in Examples 1 and 2, and this layer A was thicker than those in Examples 1 and 2. A catheter in Comparative Example 1 had a larger cross-sectional area ratio of a second layer to the first layer than those of the catheters in Examples 1 and 2. The insertion member of the catheter in Comparative Example 1 had a smaller initial roundness than those of the insertion members in Examples 1 and 2, and had a significantly decreased roundness after pressure test. This indicated that the insertion member of the catheter in Comparative Example 1 was largely deformed in a radial direction by pressure after repeated supply of a fluid into a second lumen. This deformation consequently led to flattening of the insertion member, thus causing significant friction between its inner surface and a GW, and between its outer surface and an outer tubular member.

Comparative Example 2

Comparative Example 2 employed an insertion member having one-layer structure formed from nylon 12 (Nylon 12, Rilsamid (registered trademark) AESNO MED; Arkema, melting point: 169° C., crystallinity degree: 20%, and Shore D hardness: 74). A catheter in Comparative Example 2 had both a higher initial roundness and a higher roundness after pressure test than those of the catheter in Comparative Example 1. Owing to these, the insertion member of the catheter in Comparative Example 2 was unlikely to be deformed in a radial direction by pressure even after repeated supply of a fluid into a second lumen. However, the nylon 12 had poor slidability on its surface, thus causing deterioration in slidability of the insertion member.

In Examples 1 and 2, the cross-sectional area ratio of the second layer to the first layer was 0.7 or less; at least one material included in the second layer had a higher crystallinity degree than that of at least one material included in the first layer; at least one material included in the second layer had a lower melting point than that of at least one material included in the first layer; and the insertion member, which was a multilayer tube, had an initial roundness of 92% or more. Owing to the above, the insertion member was unlikely to be deformed in a radial direction by pressure even after a fluid had been supplied into a second lumen. This prevented friction between an inner surface of the insertion member and a GW, and between an outer surface of the insertion member and an outer tubular member, thus being able to bring about excellent slidability. Furthermore, in Examples 1 and 2, a roundness after pressure test was 75% or more, and this proved that the insertion member was unlikely to be deformed in the radial direction by pressure even after repeated supply of a fluid into the second lumen.

(Measurement of Roundness 2)

Described below are the measurement results of an initial roundness and a roundness after pressure test of a catheter, such as one in FIG. 5, including a balloon connected on a distal side of a second lumen. The measurement was performed with an insertion member and an outer tubular member having the balloon that were respectively prepared. Firstly prepared by co-extrusion was the insertion member of a tubular shape that had a first layer and a second layer having a layer A and a layer B. These layers constituted three-layer structure in which the first layer, the layer B and the layer A were arranged in order from the outside in a radial direction. The prepared insertion member was subjected to an annealing treatment at 80° C. for 1 hour. The first layer was a nylon 12 elastomer (will be described in detail). The layer B was linear low-density polyethylene (LLDPE, Plexar (registered trademark) PX3080; Equistar Chemical, melting point: 127° C., and crystallinity degree: 40%). The layer A was high-density polyethylene (HDPE, Novatec (registered trademark) HB530; Japan Polyethylene Corporation, melting point: 136° C., crystallinity degree: 75%, and Shore D hardness: 71) or was polypropylene (PP, E111G; Prime Polymer Co., Ltd., melting point: 160° C., crystallinity degree: 60%, and Shore D hardness: 67). The prepared insertion member had an outer diameter of 0.55 mm and an inner diameter of 0.45 mm. From outer diameters and thicknesses of the first layer and the second layer were respectively determined cross-sectional areas of the first layer and the second layer, and from these cross-sectional areas was calculated a cross-sectional area ratio of the second layer to the first layer. In addition, a major axis outer diameter and a minor axis outer diameter of the insertion member were measured on a cross-section perpendicular to an axial direction of the insertion member, and from these measured diameters was calculated the initial roundness.

The outer tubular member was prepared by extrusion molding with a nylon 12 elastomer (Nylon 12 elastomer, PEBAX (registered trademark) 7233 SA 01 MED; Arkema, melting point: 174° C., crystallinity degree: 17%, and Shore D hardness: 69). The prepared outer tubular member had an outer diameter of 0.85 mm and an inner diameter of 0.70 mm. At a tip of this outer tubular member was joined the balloon. The balloon was prepared by blow molding with the same nylon 12 elastomer as that of the outer tubular member. The prepared balloon had an outer diameter of 2.0 mm, a length of 15 mm, and a thickness of 15 μm at a straight tube part thereof.

A pressure test was performed by the same steps as described above except that the outer tubular member having the balloon was disposed outside the insertion member in the radial direction and the RBP was set to be 14 atm. The core material was a φ0.36 mm stainless steel core material resembling a GW. After the pressure test, a major axis outer diameter and a minor axis outer diameter of the insertion member were measured, and from the measured diameters was calculated the roundness after pressure test. This measurement was performed at the same point where the major axis outer diameter and the minor axis outer diameter of the insertion member had been measured upon the calculation of the initial roundness.

The composition, the initial roundness and the roundness after pressure test of the insertion member are shown in Table 2.

TABLE 2

| | | | | Example 3 | Example 4 | Example 5 | Example 6 | Example 7 |
|---|---|---|---|---|---|---|---|---|
| Composition | First Layer | | Material | Nylon 12 Elastomer | Nylon 12 Elastomer | Nylon 12 Elastomer | Nylon 12 Elastomer | Nylon 12 Elastomer |
| | | | Melting Point (° C.) | 174 | 174 | 174 | 174 | 174 |
| | | | Crystallinity Degree (%) | 18 | 17 | 17 | 17 | 17 |
| | | | Thickness (μm) | 37 | 37 | 34 | 31 | 31 |
| | | | Shore D Hardness | 73 | 69 | 69 | 69 | 69 |
| | | | Cross-sectional Area (mm$^2$) | 0.0596 | 0.0605 | 0.0534 | 0.0521 | 0.0504 |
| | Second Layer | Layer B | Material | LLDPE | LLDPE | LLDPE | LLDPE | LLDPE |
| | | | Melting Point (° C.) | 127 | 127 | 127 | 127 | 127 |
| | | | Crystallinity Degree (%) | 40 | 40 | 40 | 40 | 40 |
| | | | Shore D Hardness | — | — | — | — | — |
| | | | Thickness (μm) | 7 | 7 | 7 | 7 | 7 |
| | | Layer A | Material | HDPE | HDPE | HDPE | HDPE | PP |
| | | | Melting Point (° C.) | 136 | 136 | 136 | 136 | 160 |
| | | | Crystallinity Degree (%) | 75 | 75 | 75 | 75 | 60 |
| | | | Shore D Hardness | 71 | 71 | 71 | 71 | 67 |
| | | | Thickness (μm) | 6 | 6 | 9 | 12 | 12 |
| | | | Cross-sectional Area (mm$^2$) | 0.0189 | 0.0189 | 0.0248 | 0.0279 | 0.0279 |
| | | | Cross-sectional Area Ratio of Second Layer to First Layer | 0.317 | 0.313 | 0.465 | 0.535 | 0.554 |
| Initial State | | | Major Axis Outer Diameter (mm) | 0.554 | 0.556 | 0.556 | 0.563 | 0.557 |
| | | | Minor Axis Outer Diameter (mm) | 0.546 | 0.546 | 0.540 | 0.539 | 0.541 |
| | | | Initial Roundness (%) | 98.6 | 98.2 | 97.1 | 95.7 | 97.1 |
| After Pressure Test | | | Major Axis Outer Diameter (mm) | 0.560 | 0.563 | 0.567 | 0.580 | 0.573 |
| | | | Minor Axis Outer Diameter (mm) | 0.539 | 0.538 | 0.529 | 0.522 | 0.525 |
| | | | Roundness After Pressure Test (%) | 96.3 | 95.6 | 93.3 | 90.0 | 91.6 |

| | | | | Comparative Example 3 | Comparative Example 4 | Comparative Example 5 | Comparative Example 6 |
|---|---|---|---|---|---|---|---|
| Composition | First Layer | | Material | Nylon 12 Elastomer | Nylon 12 Elastomer | Nylon 12 Elastomer | Nylon 12 Elastomer |
| | | | Melting Point (° C.) | 174 | 174 | 174 | 174 |
| | | | Crystallinity Degree (%) | 18 | 17 | 17 | 17 |
| | | | Thickness (μm) | 50 | 50 | 28 | 28 |
| | | | Shore D Hardness | 73 | 69 | 69 | 69 |
| | | | Cross-sectional Area (mm$^2$) | 0.0790 | 0.0790 | 0.0459 | 0.0460 |

TABLE 2-continued

|  |  |  |  |  |  |  |  |
|---|---|---|---|---|---|---|---|
|  | Second Layer | Layer B | Material | — | — | LLDPE | LLDPE |
|  |  |  | Melting Point (° C.) | — | — | 127 | 127 |
|  |  |  | Crystallinity Degree (%) | — | — | 40 | 40 |
|  |  |  | Shore D Hardness | — | — | — | — |
|  |  |  | Thickness (μm) | — | — | 7 | 7 |
|  |  | Layer A | Material | — | — | HDPE | PP |
|  |  |  | Melting Point (° C.) | — | — | 136 | 160 |
|  |  |  | Crystallinity Degree (%) | — | — | 75 | 60 |
|  |  |  | Shore D Hardness | — | — | 71 | 67 |
|  |  |  | Thickness (μm) | — | — | 15 | 15 |
|  |  | Cross-sectional Area (mm$^2$) |  | — | — | 0.0326 | 0.0327 |
|  |  | Cross-sectional Area Ratio of Second Layer to First Layer |  | — | — | 0.710 | 0.711 |
| Initial State | Major Axis Outer Diameter (mm) |  |  | 0.552 | 0.552 | 0.572 | 0.568 |
|  | Minor Axis Outer Diameter (mm) |  |  | 0.547 | 0.548 | 0.528 | 0.534 |
|  | Initial Roundness (%) |  |  | 99.1 | 99.3 | 92.3 | 94.0 |
| After Pressure Test | Major Axis Outer Diameter (mm) |  |  | 0.555 | 0.558 | 0.631 | 0.647 |
|  | Minor Axis Outer Diameter (mm) |  |  | 0.545 | 0.543 | 0.469 | 0.455 |
|  | Roundness After Pressure Test (%) |  |  | 98.2 | 97.3 | 74.3 | 70.3 |

Example 3

Example 3 employed an insertion member in which thicknesses of a first layer, a layer B and a layer A were 37 μm, 7 μm and 6 μm respectively. The first layer was formed from a nylon 12 elastomer (Nylon 12 elastomer, PEBAX (registered trademark) 7433 SA 01 MED; Arkema, melting point: 174° C., crystallinity degree: 18%, and Shore D hardness: 73). A catheter in Example 3 had a smaller cross-sectional area ratio of a second layer to the first layer than that of a catheter in Comparative Example 5. The insertion member of the catheter in Example 3 had both a high initial roundness and a high roundness after pressure test.

Example 4

Example 4 employed an insertion member in which a thickness of a first layer was 37 μm. The first layer was formed from a nylon 12 elastomer (Nylon 12 elastomer, PEBAX (registered trademark) 7233 SA 01 MED; Arkema, melting point: 174° C., crystallinity degree: 17%, Shore D hardness: 69) that was a different material from that in Example 3. A catheter in Example 4 also had a smaller cross-sectional area ratio of a second layer to the first layer than that of a catheter in Comparative Example 5. The insertion member of the catheter in Example 4 had a high initial roundness and a high roundness after pressure test.

Example 5

Example 5 employed an insertion member in which thicknesses of a first layer and a layer A were 34 μm and 9 μm respectively. The layer A was thicker than that in Example 4. A catheter in Example 5 had, like Examples 3 and 4, a smaller cross-sectional area ratio of a second layer to the first layer than that of a catheter in Comparative Example 5. The insertion member of the catheter in Example 5 had a high initial roundness and a high roundness after pressure test.

Example 6

Example 6 employed an insertion member in which thicknesses of a first layer and a layer A were 31 μm and 12 μm respectively. The layer A was thicker than that in Example 5. A catheter in Example 6 had, like Examples 3 to 5, a cross-sectional area ratio of a second layer to the first layer of 0.7 or less. The insertion member of the catheter in Example 6 had also an initial roundness of 92% or more and a roundness after pressure test of 75% or more.

Example 7

Example 7 employed an insertion member in which thicknesses of a first layer and a layer A were 31 μm and 12 μm respectively. The layer A was formed from polypropylene (PP, E111G; Prime Polymer Co., Ltd., melting point: 160° C., crystallinity degree: 60%, and Shore D hardness: 67) that was a different material from that in Example 6. The layer A of a catheter in Example 7 was formed from the different material from those of the catheters in Examples 3 to 6, but the catheter in Example 7 had a smaller cross-sectional area ratio of a second layer to the first layer than that of a catheter in Comparative Example 6. The insertion member of the catheter in Example 7 had a higher initial roundness and a higher roundness after pressure test than those of an insertion member of the catheter in Comparative Example 6.

Comparative Example 3

Comparative Example 3 employed a one-layer structure insertion member having a thickness of 50 μm. The insertion member was formed from a nylon 12 elastomer (Nylon 12 elastomer, PEBAX (registered trademark) 7433 SA 01 MED; Arkema, melting point: 174° C., crystallinity degree: 18%, Shore D hardness: 73). The insertion member of a catheter in Comparative Example 3 had both a high initial roundness and a high roundness after pressure test. Owing to these, the insertion member was unlikely to be deformed in a radial direction by pressure even after repeated supply of a fluid into a second lumen. However, the nylon 12 had poor slidability on its surface, thus causing deterioration in slidability of the insertion member.

Comparative Example 4

Comparative Example 4 employed a one-layer structure insertion member having a thickness of 50 μm. The insertion member was formed from a nylon 12 elastomer (Nylon 12 elastomer, PEBAX (registered trademark) 7233 SA 01 MED; Arkema, melting point: 174° C., crystallinity degree: 17%, Shore D hardness: 69). Like the catheter in Comparative Example 3, the insertion member of a catheter in Comparative Example 4 had both a high initial roundness and a high roundness after pressure test. Owing to these, the insertion member was unlikely to be deformed in a radial direction. However, the nylon 12 had poor slidability on its surface, thus causing deterioration in slidability of the insertion member.

Comparative Example 5

Comparative Example 5 employed an insertion member in which thicknesses of a first layer and a layer A were 28 μm and 15 μm respectively. This first layer was thinner than that in Example 6, and this layer A was thicker than that in Example 6. The first layer was formed from a nylon 12 elastomer (Nylon 12 elastomer, PEBAX (registered trademark) 7233 SA 01 MED; Arkema, melting point: 174° C., crystallinity degree: 17%, Shore D hardness: 69). A catheter in Comparative Example 5 had a high cross-sectional area ratio of a second layer to the first layer. The insertion member of the catheter in Comparative Example 5 had a smaller initial roundness than that of the insertion member of the catheter in Example 6, and had a significantly decreased roundness after pressure test. This indicated that the insertion member of the catheter in Comparative Example 5 was largely deformed in a radial direction by pressure after repeated supply of a fluid into a second lumen. This deformation consequently led to flattening of the insertion member, thus causing significant friction between its inner surface and a GW, and between its outer surface and an outer tubular member.

Comparative Example 6

Comparative Example 6 employed an insertion member in which thicknesses of a first layer and a layer A were 28 μm and 15 μm respectively. The layer A was thicker than that in Example 7. A catheter in Comparative Example 6 had a high cross-sectional area ratio of a second layer to the first layer. The insertion member of the catheter in Comparative Example 6 had a lower initial roundness and a lower roundness after pressure test than those of the insertion member of the catheter in Example 7. This indicated that the insertion member of the catheter in Comparative Example 6 was largely deformed in a radial direction by pressure after repeated supply of a fluid into a second lumen. This deformation consequently led to flattening of the insertion member, thus deteriorating slidability of the insertion member.

From the above, even with an outer tubular member having a balloon, an insertion member, which is a multilayer tube, having the following composition is unlikely to be deformed in a radial direction by pressure and therefore can achieve excellent slidability even after a fluid is supplied into a second lumen: a cross-sectional area ratio of a second layer to a first layer is 0.7 or less; at least one material included in the second layer has a higher crystallinity degree than that of at least one material included in the first layer; and at least one material included in the second layer has a lower melting point than that of at least one material included in the first layer.

The results of Examples 3 and 4 show that a first layer including at least one material having high Shore hardness can conceivably increase roundness after pressure test. The results of Examples 4 to 6 show that an insertion member having a small cross-sectional area ratio of a second layer to a first layer tends to achieve high initial roundness and high roundness after pressure test. The results of Examples 6 and 7 show that a layer A can be formed from not only HDPE but also a polyolefin-based resin such as PP.

(Slidability Test of Outer Tubular Member and Insertion Member)

Described below is the result of a slidability test of an outer tubular member. This test employed, as the outer tubular member, the multilayer tube prepared as the insertion member in Examples 4 to 6. Into a lumen of the outer tubular member was inserted a round core material made of SUS304 that corresponded to an insertion member. When the round core material could be inserted and slid without any resistance, an outer diameter thereof enabling such an insertion and a slide was checked. Presence of such resistance between the core material and the outer tubular member was judged by a sense of touch.

The result of the slidability test of the outer tubular member is shown in Table 3. In the test result, "A" indicates that the core material could be inserted into and slid in the outer tubular member without any resistance. "B" indicates that the core material could be inserted into and slid in the outer tubular member though with some resistance. "C" indicates that the core material could not be inserted into the outer tubular member owing to resistance to a great degree.

TABLE 3

| Outer Diameter of Core Material | Example 4 | Example 5 | Example 6 | Comparative Example 5 |
|---|---|---|---|---|
| 0.45 mm | B | B | B | C |
| 0.44 mm | A | B | B | B |
| 0.43 mm | A | A | A | B |
| 0.42 mm | A | A | A | A |

The core material having an outer diameter of 0.45 mm could be inserted, though with some resistance, into outer tubular members in Examples 4 to 6 that had equal inner diameters (0.45 mm) to the outer diameter of the core material. However, this core material could not be inserted into an outer tubular member in Comparative Example 5 owing to resistance to a great degree. The core material having an outer diameter of 0.44 mm could be inserted into and slid in the outer tubular member in Example 4 without any resistance. Further, the core material having an outer diameter of 0.43 mm could be inserted into and slid in the outer tubular members in Examples 4 to 6 but with some resistance in Comparative Example 5.

From the above, a smaller cross-sectional area ratio of a second layer to a first layer brings about higher initial roundness. Higher initial roundness enables insertion and slide of a member having a larger outer diameter. That is, a smaller cross-sectional area ratio of a second layer to a first layer tends to bring about more improved slidability.

DESCRIPTION OF REFERENCE SIGNS

1: a catheter
2: a shaft
3: an insertion member
4: an outer tubular member
5: a first lumen
6: a second lumen
7: a third lumen
8: a balloon
10: a stiffener
20: a hub
21: a fluid injection part
22: a treatment part
31: a first layer
32: a second layer 33: a layer A
34: a layer B Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

The invention claimed is:

1. A catheter having a distal side and a proximal side comprising:
   a shaft having an outer tubular member, and
   an insertion member wherein at least a part of the insertion member in an axial direction thereof is disposed in the outer tubular member,
   at least one of the outer tubular member or the insertion member is a multilayer tube having a first layer and a second layer laminated with the first layer,
   wherein in a cross-section that is perpendicular to an axial direction of the multilayer tube, a ratio of a cross-sectional area of the second layer to a cross-sectional area of the first layer (cross-sectional area of the second layer/cross-sectional area of the first layer) is 0.7 or less,
   a material constituting the second layer has a higher degree of crystallinity than that of a material constituting the first layer,
   wherein the material constituting the second layer has a lower melting point than that of the material constituting the first layer, and
   wherein in the cross-section that is perpendicular to the axial direction of the multilayer tube, an initial roundness calculated by equation (1) is 92% or more,
   wherein equation (1) is:

$$\text{initial roundness (\%)} = (\text{a minor axis outer diameter of the multilayer tube/a major axis outer diameter of the multilayer tube}) \times 100, \text{ and} \quad (1)$$

wherein the outer tubular member and the insertion member are relatively movable in a distal and proximal direction.

2. The catheter according to claim 1, wherein the second layer is disposed more inside in a radial direction than the first layer.

3. The catheter according to claim 1, wherein the insertion member is the multilayer tube.

4. The catheter according to claim 3, wherein the insertion member has a first lumen for a guide wire.

5. The catheter according to claim 3, wherein the shaft has a second lumen for flow passage of a fluid and wherein the second lumen is disposed between the outside of the insertion member and the inside of the outer tubular member.

6. The catheter according to claim 5, wherein in a cross-section that is perpendicular to the axial direction of the insertion member, and after a pressure test that follows, a roundness of the insertion member calculated by the following equation (2) is of 75% or more, after the pressure test, wherein the pressure test is defined by (i)-(v),
   (i) disposing a core material within the first lumen,
   (ii) placing the catheter under a 1 atm (atmospheric pressure) and 37° C. water environment,
   (iii) applying pressure of rated burst pressure (RBP)+1 atm (atmospheric pressure) to within the second lumen for 30 seconds,
   (iv) depressurizing the pressure within the second lumen to 1 atm (atmospheric pressure), and
   (v) repeating the above (iii) to (iv) 20 times;
   wherein equation (2) is:

$$\text{roundness after pressure test (\%)} = (\text{a minor axis outer diameter of the insertion member after the pressure test/a major axis outer diameter of the insertion member after the pressure test}) \times 100 \quad (2)$$

wherein the minor axis outer diameter and the major axis outer diameter of the insertion member after the pressure test are measured at the same point where the minor axis outer diameter and the major axis outer diameter of the insertion member are measured upon the calculation of the initial roundness.

7. The catheter according to claim 5, wherein when the fluid is supplied with the rated burst pressure (RBP) into the second lumen, and an outer diameter reduction rate of the insertion member at a point where an outer diameter of the insertion member becomes smallest is within 10%.

8. The catheter according to claim 5, wherein the point where the outer diameter of the insertion member becomes smallest is inside the second lumen.

9. The catheter according to claim 5, wherein the second lumen is provided on the distal side of the shaft.

10. The catheter according to claim 5, comprising a balloon connected on the distal side of the second lumen.

11. The catheter according to claim 5, wherein the shaft has a third lumen for flow passage of a fluid, into which a fluid is supplied, and wherein the catheter has a balloon which is connected to the third lumen, on the distal side of the shaft.

12. The catheter according to claim 1, wherein a ratio of a Shore hardness of the material constituting the first layer to a Shore hardness of the material constituting the second layer (Shore hardness of the material constituting the first layer/Shore hardness of the material constituting the second layer) is 0.9 or more.

13. The catheter according to claim 1, wherein the material constituting the first layer and the material constituting the second layer are a thermoplastic resin.

14. The catheter according to claim 1, wherein the material constituting the first layer is a polyamide-based resin.

15. The catheter according to claim 1, wherein the material constituting the second layer is a polyolefin-based resin.

16. The catheter according to claim 15, wherein the polyolefin-based resin is a high-density polyethylene resin or a polypropylene resin.

17. The catheter according to claim 1, wherein the second layer has a layer A, and a layer B laminated with the layer A, and the layer B joins the first layer and the layer A.

18. The catheter according to claim 17, wherein a material constituting the layer B is a linear low-density polyethylene resin.

19. A method for producing the catheter according to claim 1, the method comprising a step of producing by co-extrusion molding the multilayer tube having the first layer and the second layer laminated with the first layer.

* * * * *